United States Patent [19]
Naramoto et al.

[11] 3,944,613
[45] Mar. 16, 1976

[54] PROCESS FOR PREPARING DIPHENYLAMINE FROM ANILINE

[75] Inventors: Isao Naramoto; Tatsuo Kyuma; Giichi Akazome, all of Kyoto, Japan

[73] Assignee: New Japan Chemical Company, Limited, Japan

[22] Filed: Sept. 6, 1974

[21] Appl. No.: 503,700

[30] Foreign Application Priority Data
  Sept. 10, 1973  Japan.............................. 48-102340

[52] U.S. Cl............................. 260/576; 252/455 R
[51] Int. Cl.².......................................... C07C 87/54
[58] Field of Search................. 260/576; 252/455 R

[56] References Cited
UNITED STATES PATENTS
3,118,944  1/1964  Addis................................ 260/576

OTHER PUBLICATIONS
OHTA et al. Chem. Abstracte 49 Col. 13135 c,d.
OHTA et al. Chem Abstracts 44 Col. 922 th, i Col. 9225 b.c. Col. 9226 a, b, c.
Rose et al. The Condensed Chemical Dictionary 1961; Rheinhold Publishing Co. N.Y. pp. 636, 637.
OHTA Chem. Abstracts 50 Col. 3263 p.

*Primary Examiner*—Arthur P. Demers
*Attorney, Agent, or Firm*—McGlew and Tuttle

[57] ABSTRACT

In repairing diphenylamine by reacting aniline in a liquid phase in the presence of a catalyst at a temperature of about 320° to about 370°C, a process which is characterized in that said catalyst is an amorphous synthetic silica-alumina catalyst containing 5 to 50% by weight of alumina.

6 Claims, No Drawings

PROCESS FOR PREPARING DIPHENYLAMINE FROM ANILINE

This invention relates to a process for preparing diphenylamine from aniline, more particularly to a process for preparing diphenylamine from aniline by pressure liquid phase process.

Pressure liquid phase process and gas phase process are known as processes for preparing diphenylamine from aniline. In the known pressure liquid phase process aniline is reacted at a temperature ranging from about 250° to about 400°C at such pressure that aniline can be maintained in liquid state in the presence of hydrochloric acid, boron trifluoride or like mineral acid catalyst, or Lewis acid catalyst. According to this process remarkable corrosion to the apparatus is unavoidable, since a large amount of mineral acid catalyst is used at a high reaction temperature. It is therefore necessary to employ an acid- and pressure-resistant reactor. Moreover there is a need to separate the acid catalyst from the product after the reaction. The use of Lewis acid catalyst also requires a corrosion-resistant reactor and yields a large amount of tar-like by-product.

To overcome the above drawbacks it has been proposed to use a natural clay as a catalyst in place of the acid catalysts. However, the clay catalysts are poor in catalytic activity and duration of catalytic activity as compared with acid catalysts. In fact the process in which the clay catalyst is used is disadvantageous in that the catalyst used is especially of a short duration and hardly serviceable for a prolonged period and is therefore infeasible on an industrial scale. In addition the process has another drawback that the catalyst which is a natural clay is not always available with a uniform quality.

Although the gas phase process does not necessitate a corrosion- and pressure-resistant reactor since it uses a solid acid catalyst, the catalyst gets degraded promptly and need be regenerated frequently due to the deposition of tar-like by-products on the catalyst.

A main object of this invention is to overcome the foregoing drawbacks of pressure liquid phase process for preparing diphenylamine from aniline.

Another object of this invention is to provide a pressure liquid phase process for preparing diphenylamine from aniline without a tar-like by-product in a high yield, by using a solid catalyst having an excellent catalytic activity.

Other objects of this invention will become apparent from the following description.

The above objects can be accomplished by using an amorphous synthetic silica-alumina catalyst containing 5 to 50% by weight of alumina in a process for preparing diphenylamine by reacting aniline in a liquid phase.

Our researches have revealed that a solid material of the amorphous synthetic silica-alumina containing 5 to 50% by weight of alumina has outstanding characteristics for use as a catalyst in preparing diphenylamine from aniline. More specifically we found that the amorphous synthetic silica-alumina has higher catalytic activity and longer duration of catalytic activity than the catalyst of the natural clay and that the use of the amorphous synthetic silica-alumina catalyst, which is especially of very long duration of activity, makes it possible to produce diphenylamine from aniline in a high yield for a prolonged period of time. The present invention has been accomplished based on these novel findings.

The silica-alumina catalyst to be used in this invention has three features: it contains 5 to 50% by weight of alumina, it is amorphous and it is a synthetic product. The term "amorphous" herein used refers to the properties of the catalyst that when subjected to X-ray diffractiometry the catalyst does not exhibit any sharp peak but displays broad peaks and that it is not crystalline as examined by X-ray diffractiometry.

The silica-alumina catalyst to be used in the present invention must contain 5 to 50% by weight of alumina. If the alumina content is less than 5% by weight or in excess of 50% by weight, the catalyst is very low in its activity and fails to yield diphenylamine efficiently. The alumina content is preferably in the range of 10 to 40% by weight, most preferably in the range of 10 to 30% by weight.

The amorphous synthetic silica-alumina catalysts per se are already known; they are generally used, for example, for cracking of petroleum. Such catalysts used for cracking of petroleum are ready for use in this invention, examples being "N-631H" and "N-631L", product of Nikki Chemical Co., Ltd., Japan.

The silica-alumina catalyst of this invention can be synthetically produced by various methods. One of examples thereof is disclosed in "Chemical Industries (Kogyo Kagaku Kaishi)" Vol. 56 (1953) on page 176.

The synthetic silica-alumina catalyst of this invention can be produced, for example, by washing a hydrogel of silica and alumina with water, drying, and then calcining the dried hydrogel. The hydrogel of silica and alumina can be produced, for example, by cogelation method, incorporation method or mixing method. According to the cogelation method, an aqueous solution of the siliceous material and an aqueous solution of the aluminous material are mixed together to prepare a silica-alumina hydrogel. Incorporation method is one in which a silica-hydrogel is prepared and then incorporated with an alumina gel by adding an aqueous solution of the aluminous material to the silica hydrogel, or an alumina hydrogel is previously prepared and then incorporated with a silica hydrogel by adding an aqueous solution of siliceous material to the alumina hydrogel. According to mixing method, a silica-alumina gel is produced by preparing silica hydrogel and alumina hydrogel separately, and mixing the hydrogels together. Usable as the siliceous material are water-soluble silicates of alkali metals such as lithium, potassium, sodium, etc., preferably of potassium and sodium. A specific example is water glass (comprising $Na_2O$ and $SiO_2$ in the molar ratio of about 1 : 2–4). Examples of the aluminous material are water-soluble aluminum salts or aluminates. Exemplary of aluminum salts are aluminum sulfate, aluminum nitrate, aluminum chloride, potassium alum, sodium alum, etc. Examples of aluminates are alkali metal salts of aluminic acid such as sodium aluminate, potassium aluminate, etc.

The cogelation method, incorporation method and mixing method will be described below in detail.

Cogelation method

An aqueous solution of siliceous material having an $SiO_2$ concentration of 5 to 30%, preferably of 10 to 20%, and an aqueous solution of aluminous material having an $Al_2O_3$ concentration of 2 to 10%, preferably of about 3 to 7%, are mixed together in the silica to alumina ratio of 90–60% to 10–40%, with vigorous agitation at 10° to 40°C, preferably at 20° to 30°C, to precipitate a silica-alumina hydrogel. According to this method, it is necessary to adjust the mixture of aqueous solution to a pH of 2 to 10, preferably to about 3 to 7. The silica-alumina hydrogel is then aged at the pH of the above-mentioned range. The aging is effected at atmospheric pressure at a temperature of up to 110°C, preferably approximately at room temperature to 60°C, for 3 to 20 hours, preferably for 5 to 15 hours. The silica-alumina hydrogel thus aged is then washed several times with a dilute alkaline aqueous solution for example of ammonia or inorganic ammonium salt and is finally washed with water and filtered. The hydrogel is subsequently dried, as such or after shaping, at 100° to 150°C. The dried silica-alumina hydrogel is thereafter calcined in air at 400° to 700°C, preferably at 500° to 550°C for 1 to 6 hours, advantageously for 2 to 3 hours, whereby the desired catalyst is obtained. If the hydrogel is calcined at a temperature of below 400°C or above 700°C, satisifactory catalytic activity will be unavailable.

Incorporation method

A mineral acid such as sulfuric acid, hydrochloric acid or nitric acid is added to an aqueous solution of siliceous material to adjust the pH of the solution to 2 to 7, preferably to 3 to 6 and to prepare a silica hydrogel, which is then aged in the same manner as in the cogelation method described above. A specified amount of aqueous solution of aluminous material are added to the hydrogel and the pH of the resulting mixture is adjusted to 3 to 10, preferably to 5 to 7 and to thereby incorporate an alumina hydrogel into the silica hydrogel. The resulting silica-alumina hydrogel is then treated in the same manner as in cogelation method to obtain the desired silica-alumina catalyst.

Mixing method

An aqueous solution of aluminous material is adjusted to a pH of 6 to 10 to prepare an alumina hydrogel, which is aged at pH of 6 to 10, preferably at room temperature to 60°C, and is thereafter washed. On the other hand, a mineral acid is added to an aqueous solution of siliceous material to adjust the pH to 2 to 8, advantageously to 3 to 6, and to prepare a silica hydrogel, which is then similarly aged at a pH of 3 to 6 at a temperature of up to 110°C and thereafter washed to prepare a silica hydrogel. The silica hydrogel and alumina hydrogel thus prepared separately are mixed together in a predetermined ratio, and the mixture is mechanically kneaded for 1 to 10 hours, preferably for 3 to 5 hours. Subsequently, the mixture is dried and calcined under the same conditions as in the foregoing two methods.

The silica-alumina catalyst to be used in this invention may contain small amounts of impurities, for example up to 0.2% of iron, magnesium and sodium oxides. The silica-alumina catalyst may be in a wide variety of shapes, e.g. in the shape of powder, tablets or granules as desired.

The reaction for preparing diphenylamine by this invention is represented by the following equation.

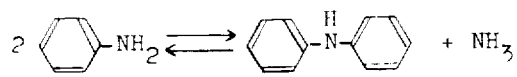

The above reaction of this invention is conducted under the temperature condition of about 320° to about 370°C. At temperatures below about 320°C, the reaction proceeds slowly, whereas at temperatures in excess of about 370°C an objectionable tar-like byproduct is produced in an increased amount and the reaction system requires a higher temperature to maintain aniline, the starting material, in liquid state. In order to prevent deposition of tar on the catalyst used and to keep the catalyst active for a prolonged period of time, the reaction must be carried out in liquid phase, usually employing a closed reactor such as autoclave. The reaction is conducted while releasing the ammonia which is evolved in the course of reaction, wereby the reaction can be effected favorably. Accordingly, the pressure applied to the system in practicing this invention is such that the reaction phase can be maintained in liquid state under the foregoing temperature conditions while the resulting ammonia is being withdrawn from the system. The reaction pressure rises in proportion to the reaction temperature and lowers as the mole fraction ratio of aniline decreases with the progress of reaction. The reaction pressure corresponds to the saturated vapor pressure of aniline at the reaction temperature and is usually in the range of 13 to 32 kg/cm$^2$ at the reaction temperature of the above-mentioned range.

The process of this invention can be practiced either in a batch process or a mixed-bed process.

When the present invention is practiced in the batch process, the catalyst is used in an amount usually of 30 to 120% by weight, preferably of 50 to 80% by weight, based on the starting material, i.e. aniline.

The present invention is practiced continuously by employing the fixed-bed process in which aniline is continuously fed to a fixed bed of catalyst. For this operation, it is preferably to maintain aniline in contact with the catalyst for an apparent contact time of 0.5 to 3.0 hours. The apparent contact time is defined as follows:

$$\text{Apparent contact time} = \frac{\text{Volume of catalyst (liter)}}{\text{Feed rate of aniline (liter/hour)}}$$

According to the process of this invention, dephenylamine, the desired product, can be readily isolated from the reaction mixture by distilling the mixture. In the batch process, the catalyst is first removed by filtering from the reaction mixture resulting from the reaction, and the liquid obtained is distilled, whereby unreacted aniline is first recovered and then diphenylamine is obtained as the desired product, leaving a tar-like substance as a residue.

According to the fixed-bed process, the gaseous reaction mixture resulting from the reaction is first condensed and then the condensate is subjected to distillation to recover unreacted aniline and to obtain desired diphenylamine. The reason why diphenylamine can be obtained by such a simple procedure as distillation is mainly attributable to the fact that the present process hardly entails formation of other byproducts.

In this process unreacted aniline recovered can be used for next reaction as the starting material without any refining.

The catalyst used in this invention is of a long duration of activity and is hardly deteriorated in its catalytic activity even when used continuously for 2,000 hours. It is able to produce diphenylamine in a very high yield, permitting formation of only a very small amount of byproduct. Moreover, the catalyst of this invention is characterized in that it is easy to regenerate. When the catalyst has been impaired slightly in its activity after using for a long period of more than 2,000 hours, it can be regenerated almost to its original activity if heated in air at about 450° to 500°C.

EXAMPLE 1

Into a 200-ml autoclave were placed 50 g of each of the finely divided catalysts given in Table 1 below and 100 g of aniline, and the reactor was sealed after replacing the interior air with nitrogen gas. The aniline was reacted at 340°C for 6 hours. The reaction pressure which was initially 20 kg/cm$^2$ rose to 23 to 36 kg/cm$^2$ at the final stage of reaction. After the reaction, the reaction mixture was cooled and withdrawn from the autoclave. After the catalyst was filtered off, the reaction mixture was analyzed by gas chromatography to determine the composition. The results are shown in Table 1.

Table 1

| No. | Kind of catalyst | Composition of reaction mixture (% by weight) | | |
|---|---|---|---|---|
| | | Diphenylamine | Aniline | Others |
| 1 | Silica-alumina catalyst | 46.5 | 52.2 | 1.3 |
| 2 | Activated clay | 29.9 | 68.3 | 1.8 |
| 3 | Zeolite | 19.5 | 79.9 | 0.6 |
| 4 | Solid phosphoric acid-diatomaceous earth | 11.0 | 88.5 | 0.5 |
| 5 | Alumina-boria catalyst | 15.8 | 83.5 | 0.7 |

The catalysts listed in Table 1 are as follows:

Silica-alumina catalyst: "N-631H", product of Nikki Chemical Co., Ltd., Japan, alumina content: 28% by weight, amorphous synthetic catalyst.

Activated clay: "Galleon earth", product of Mizusawa Chemical Co., Ltd., Japan

Zeolite: Prepared by immersing "Molecular Sieves 13X", trade mark, product of Union Carbide Corporation, U.S.A. in aqueous solution of calcium nitrate for exchange of Ca$^{++}$, followed by calcining at 450°C for 2 hours.

Solid phosphoric acid-diatomaceous earth: "N-501", product of Nikki Chemical Co., Ltd., Japan.

Alumina-boria catalyst: Prepared by immersing "γ-alumina", product of Nikki Chemical Co., Ltd., Japan, in boric acid, followed by calcining at 400° to 450°C for 2 hours.

Table 1 indicates that the use of silica-alumina catalyst (No. 1) of this invention gave a product with a high diphenylamine content of 46.5% by weight in contrast with fairly low yields achieved by the use of other catalysts (Nos. 2 to 5).

EXAMPLE 2

Three kinds of silica-alumina catalysts containing 27 to 30% by weight of alumina were prepared by the following three methods.

Catalyst 1

800 ml of water glass having a molar ratio of SiO$_2$ : Na$_2$O of 2 : 1 and containing 70 g of SiO$_2$ and 1,200 ml of an aqueous solution of aluminum sulfate containing 38.8 g of Al$_2$SO$_4$ (Al$_2$O$_3$ content is 30 g) were mixed together with vigorous agitation, and the pH of the mixture was finally adjusted to 6 to prepare a silica-alumina hydrogel, which was then aged at 40°C for 16 hours, washed, dried at 110°C and calcined at 500° to 550°C for 3 hours.

Catalyst 2

The same amounts of the same aqueous solutions of water glass and aluminum sulfate as in the case of Catalyst 1 were used. Sulfuric acid was added to the water glass to adjust the pH to 4 and to prepare a silica hydrogel, which was aged at 40°C for 16 hours. The aqueous solution of aluminum sulfate was then added to the aged hydrogel, and the pH was adjusted to 7 to incorporate an alumina hydrogel into the silica hydrogel. The resulting silica-alumina hydrogel was subsequently aged at 30°C for 10 hours and thereafter dried and calcined in the same manner as Catalyst 1.

Catalyst 3

Sulfuric acid was added to the same aqueous solution of water glass as in the case of Catalyst 1 to adjust the pH to 4 and to form a silica hydrogel, which was aged at 40°C for 16 hours and washed. From the same aqueous solution of aluminum sulfate as above and sodium hydroxide, an alumina hydrogel was prepared at a pH of 7 to 8 and was aged under the same conditions as the silica hydrogel, followed by washing. The hydrogels thus obtained were mixed together in the alumina to silica ratio by weight of 3 : 7, and the mixture was kneaded by a ball mill for 5 hours, and dried and calcined under the same conditions as Catalysts 1 and 2.

Diphenylamine was prepared using each of the above catalysts and following the same procedure as in Example 1. The results are given in Table 2 below.

Table 2

| Kind of catalyst | Composition of reaction mixture | | |
|---|---|---|---|
| | Diphenylamine | Aniline | Others |
| Catalyst 1 | 42.7 | 56.1 | 1.1 |
| "2 | 42.2 | 56.3 | 1.5 |
| "3 | 40.6 | 58.2 | 1.2 |

EXAMPLE 3

Water glass having a molar ratio of SiO$_2$ : Na$_2$O of 2 : 1 and an aqueous solution of aluminum nitrate were mixed together and the same procedure was followed to prepare various kinds of catalyst having alumina content shown in Table 3 below, and the same procedure as in Catalyst 1 in Example 2 was followed to prepare various kinds of catalysts. Using each of the catalysts and in the same manner as in Example 1, diphenylamine was produced, with the results given in Table 3, which also shows the results achieved using two kinds of commercial silica-alumina catalysts (No. 9 and No. 10) to produce diphenylamine.

Table 3

| No. | Alumina content | Composition of reaction mixture(%) | | |
|---|---|---|---|---|
| | | Diphenylamine | Aniline | Others |
| 1 | 0 | 10.4 | 89.1 | 0.5 |
| 2 | 5 | 24.3 | 74.7 | 1.0 |
| 3 | 13 | 40.5 | 58.2 | 1.3 |
| 4 | 28 | 41.1 | 57.6 | 1.3 |
| 5 | 40 | 35.6 | 63.2 | 1.2 |
| 6 | 50 | 26.4 | 72.5 | 1.1 |

Table 3-continued

| No. | Alumina content | Composition of reaction mixture(%) | | |
|---|---|---|---|---|
| | | Diphenylamine | Aniline | Others |
| 7 | 75 | 9.6 | 89.9 | 0.5 |
| 8 | 100 | 5.5 | 94.3 | 0.2 |
| 9*¹⁾ | 10 – 14 | 43.7 | 55.1 | 1.2 |
| 10*²⁾ | 25 – 27 | 46.5 | 52.1 | 1.3 |

Note:
*¹⁾"N-631L", product of Nikki Chemical Co., Ltd., Japan, amorphous synthetic silica-alumina catalyst, in the form of tablets, 6 mm in diameter and 5 mm in thickness.
*²⁾"N-631H", product of Nikki Chemical Co., Ltd., Japan, amorphous synthetic silica-alumina catalyst, in the form of tablets, 6 mm in diameter and 5 mm in thickness.

EXAMPLE 4

Into a 200-ml autoclave are placed 50 g of a silica-alumina catalyst ("N-631H", product of Nikki Chemical Co., Ltd., Japan, alumina content: 25 to 27% by weight, amorphous synthetic product) crushed to 100-mesh and dried at 320° to 370°C for 1 hour and 100 g of aniline, and the air in the autoclave was replaced by nitrogen gas. The aniline was then reacted at a specified temperature for 2.5 hours. After cooling the reaction mixture, the catalyst was filtered off, and 50 g of the reaction mixture was taken out and subjected to distillation at the reduced pressure to determine the amounts of volatile component and residue. The volatile component was subjected to gas chromatography to determine the composition thereof, with the results shown in Table 4 below.

Table 4

| Temp. (°C) | Volatile oily component (%) | Residue (%) | Composition of volatile oily component (%) | | |
|---|---|---|---|---|---|
| | | | Diphenylamine | Aniline | Others |
| 320 | 97.9 | 0.4 | 20.8 | 79.1 | 0.1 |
| 355 | 96.2 | 1.2 | 34.7 | 65.1 | 0.2 |
| 370 | 94.3 | 2.4 | 45.1 | 54.1 | 0.3 |

EXAMPLE 5

Reaction was conducted in the same manner as in Example 4 except that the evolved ammonia gas was released from the autoclave when the reaction temperature reached 355°C and every 5 minutes thereafter. A small amount of aniline which escaped with the released gas was collected by a condenser and mixed with the reaction mixture after the reaction. After filtering off the catalyst from the reaction mixture, 50 g of reaction product was taken out and distilled at a reduced pressure to obtain 48.9 g of volatile oily component and 0.8 g of nonvolatile component. When analyzed by gas chromatography, the volatile component was found to be composed of 43.0% by weight of aniline, 56.6% by weight of diphenylamine and 0.4% by weight of others.

EXAMPLE 6

An apparatus for continuous reaction comprising an 800-ml cylindrical pressure-resistant vessel measuring 40 mm in inner diameter and 700 mm in height and equipped with a liquid inlet at its lower portion and with a pressure gauge and a gas and liquid outlet at its top was packed with 650 ml of silica-alumina catalyst ("N631-L", product of Nikki Chemical Co., Ltd., the same as Example 3). Aniline preheated to 345°C was continuously fed, at a rate of 300 ml/hr, to the reactor which was maintained at a temperature of 345°C and at a pressure of 19.5 to 20.0 kg/cm². The reaction product, unreacted aniline and ammonia were continuously withdrawn from the top. The reaction product thus withdrawn was treated in the same manner as in Example 4 to determine the proportions by weight of the nonvolatile and volatile components. The composition of the volatile component was also determined to calculate the content of diphenylamine as well as the ratio of byproduct to diphenylamine. To show the variations of the catalytic activity and of selectivity, Table 5 gives the content of diphenylamine in the reaction mixture and the amount of byproduct with the lapse of time.

Table 5

| Reaction time (hrs) | Diphenylamine content (% by weight) | Byproduct (% by weight) |
|---|---|---|
| 10 | 17.3 | 0.68 |
| 200 | 16.3 | 0.65 |
| 500 | 15.8 | 0.65 |
| 1000 | 15.2 | 0.62 |
| 1500 | 14.8 | 0.59 |
| 2000 | 14.6 | 0.59 |

COMPARISON EXAMPLE 1

3% by weight of graphite was added to activated clay ("galleon earth", trade mark, product of Mizusawa Chemical Co., Ltd., Japan), and the mixture was made into tablets, 6 mm in diameter and 5 mm in thickness, by compression molding. The tablets were then calcined at 500°C for 2 hours. The same procedure as in Example 6 was followed except that the catalyst thus prepared was used in place of the silica-alumina catalyst in Example 6. The results are given in Table 6 below.

Table 6

| Reaction time (hrs) | Diphenylamine content (% by weight) | Byproduct (% by weight) |
|---|---|---|
| 10 | 13.30 | 0.65 |
| 50 | 9.50 | 0.51 |
| 100 | 6.60 | 0.32 |
| 200 | 6.10 | 0.30 |

What we claim is:

1. In the process for preparing diphenylamine by reacting aniline in a liquid phase in the presence of a catalyst at a temperature of about 320° to about 370°C, the improvement wherein said catalyst comprises an amorphous synthetic silica-alumina catalyst containing 5 to 50% by weight of alumina.

2. The improved process for preparing diphenylamine from aniline as set forth in claim 1, wherein said silica-alumina catalyst contains 10 to 40% by weight of alumina.

3. The improved process for preparing diphenylamine from aniline as set forth in claim 2, wherein said silica-alumina catalyst contains 10 to 30% by weight of alumina.

4. The improved process for preparing diphenylamine from aniline as set forth in claim 1, wherein said reaction is conducted in a batch process.

5. The improved process for preparing diphenylamine from aniline as set forth in claim 4, wherein said amorphous synthetic silica-alumina catalyst is used in an amount of 30 to 120% by weight based on the aniline.

6. The improved process for preparing diphenylamine from aniline as set forth in claim 5, wherein said reaction is conducted in a fixed-bed process.

* * * * *